(12) United States Patent
Green et al.

(10) Patent No.: US 9,339,282 B2
(45) Date of Patent: May 17, 2016

(54) AUGER GUIDEWIRE

(71) Applicant: Cook Medical Technologies LLC, Bloomington, IN (US)

(72) Inventors: Sara M. Green, Bloomington, IN (US); Tyler P. Turk, Greenwood, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 243 days.

(21) Appl. No.: 13/787,274

(22) Filed: Mar. 6, 2013

(65) Prior Publication Data

US 2014/0094834 A1    Apr. 3, 2014

Related U.S. Application Data

(60) Provisional application No. 61/708,836, filed on Oct. 2, 2012.

(51) Int. Cl.
*A61B 17/22* (2006.01)
*A61D 1/02* (2006.01)
*A61M 25/09* (2006.01)
*A61B 17/3207* (2006.01)

(52) U.S. Cl.
CPC ............. *A61B 17/22* (2013.01); *A61B 17/3207* (2013.01); *A61M 25/09* (2013.01); *A61B 2017/22042* (2013.01); *A61B 2017/22044* (2013.01); *A61B 2017/22079* (2013.01); *A61B 2017/22094* (2013.01)

(58) Field of Classification Search
CPC ................. A61B 17/32002; A61B 17/320725; A61B 17/320783; A61B 17/7011; A61B 17/32037; A61B 2017/00685; A61B 17/3207; A61B 17/22044; A61B 2017/22094; A61B 10/0233; A61B 17/320758
USPC ........... 606/99, 100, 185, 159, 170–171, 107, 606/167, 180; 604/22, 164.13; 600/585, 600/564, 566, 567
See application file for complete search history.

(56) References Cited

U.S. PATENT DOCUMENTS

| | | | |
|---|---|---|---|
| 568,932 | A | 10/1896 | Wilcox |
| 3,749,085 | A | 7/1973 | Willson et al. |
| 4,471,777 | A | 9/1984 | McCorkle, Jr. |
| 4,653,496 | A | 3/1987 | Bundy et al. |
| 4,857,046 | A | 8/1989 | Stevens et al. |
| 4,883,458 | A * | 11/1989 | Shiber .............................. 604/22 |
| 4,935,025 | A | 6/1990 | Bundy et al. |
| 5,078,723 | A | 1/1992 | Dance et al. |
| 5,417,703 | A * | 5/1995 | Brown et al. .................. 606/159 |
| 5,437,266 | A | 8/1995 | McPherson et al. |
| 6,083,237 | A | 7/2000 | Huitema et al. |
| 6,824,550 | B1 | 11/2004 | Noriega et al. |
| 7,008,381 | B2 | 3/2006 | Janssens |
| 7,104,966 | B2 | 9/2006 | Shiber |
| 7,763,012 | B2 | 7/2010 | Petrick et al. |
| 7,815,580 | B2 | 10/2010 | Viswanathan |
| 7,841,994 | B2 | 11/2010 | Skujins et al. |
| 8,034,075 | B2 | 10/2011 | Dehnad |

(Continued)

*Primary Examiner* — Katherine M Shi

(74) *Attorney, Agent, or Firm* — Brinks Gilson & Lione

(57) ABSTRACT

A guidewire is provided with first and second helical members at the distal end of the guidewire. The helical members enmesh with each other in a retracted state. The second helical member is extended from the first helical member by rotating a tubular member and core member relative to each other. This causes the first and second helical members to be driven apart from each other along a helical path defined by the engagement between helical members.

20 Claims, 4 Drawing Sheets

(56) References Cited

U.S. PATENT DOCUMENTS

| | | |
|---|---|---|
| 2006/0074442 A1 | 4/2006 | Noriega et al. |
| 2007/0255183 A1 | 11/2007 | Chen |
| 2008/0097247 A1 | 4/2008 | Eskuri |
| 2008/0221601 A1 | 9/2008 | Huynh et al. |
| 2010/0082051 A1 | 4/2010 | Thorpe et al. |
| 2011/0160755 A1 | 6/2011 | McGhie |
| 2013/0066345 A1* | 3/2013 | Wilkinson .................... 606/159 |

\* cited by examiner

AUGER GUIDEWIRE

This application claims priority to U.S. Provisional Application No. 61/708,836, filed Oct. 2, 2012, which is hereby incorporated by reference herein.

BACKGROUND

The present invention relates generally to medical devices and particularly to an auger device for penetrating an occlusion.

Minimally invasive medical procedures have become common in the medical profession due to the lower risk and trauma associated with minimally invasive procedures and the lower cost compared to open surgical procedures. Minimally invasive procedures generally involve gaining access to a patient's internal vessel by puncturing the patient's skin, intermediate tissues between the skin and the vessel, and the wall of the vessel. An elongate medical instrument may then be inserted through the access site so that the distal end of the medical instrument is located within the patient's internal vessel, while the proximal end of the medical instrument remains outside the patient's body. The physician may then manipulate the proximal end of the medical instrument outside the patient's body to move and orient the distal end of the medical instrument to a location within the vessel where treatment is needed. Thus, a treatment site within a patient's vessel may be treated from outside the patient's body through a relatively small access site that is located some distance from the treatment site. By contrast, conventional open surgical procedures would require opening the tissues immediately adjacent the treatment site so that the surgeon can gain direct access to the treatment site.

One example of where minimally invasive procedures are commonly used is the treatment of stenoses and other occlusions within vessels using angioplasty techniques. Typically, angioplasty procedures are performed using a balloon-tipped catheter that may or may not have a balloon-expandable stent mounted on the balloon. In general, a physician performs an angioplasty procedure by introducing a balloon catheter into a peripheral artery (commonly one of the leg or arm arteries) and threading the catheter to the narrowed region of the artery. During this stage, the balloon is uninflated and collapsed onto the shaft of the catheter in order to present a low profile which may be passed through the arterial lumens. Once the balloon is positioned at the narrowed region of the artery, the balloon is expanded by pumping a mixture of saline and contrast solution through the catheter to the balloon. As a result, the balloon presses against the inner wall of the artery to dilate it. If a balloon-expandable stent is mounted on the balloon, the balloon inflation also serves to expand the stent and implant it in the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. Alternatively, the balloon catheter may be used to dilate a stenosis without implanting a stent. A balloon-expandable stent or self-expandable stent may then be implanted in the dilated region in a follow-up procedure. If desired, a physician may also dilate the artery and stent a second time after the stent is implanted with a balloon catheter.

However, some types of occlusions are difficult to treat with conventional angioplasty procedures. For example in the case of severe occlusions, the passageway extending through the occlusion may have become so narrow that a conventional balloon catheter and/or guidewire may not be able to pass through the occlusion. Moreover, some occlusions become completely blocked, also known as a chronic total occlusion (CTO), such that there is no longer any open passageway extending through the occlusion. In these cases, it may not even be possible to push a conventional guidewire through the center of the occlusion. In order to treat severe occlusions like these, some physicians have resorted to forcing the guidewire around the occlusion through layers of the vessel wall and then pushing the entire occlusion to the side with a balloon. However, this procedure causes undesirable trauma because the inner layers of the vessel wall where the guidewire penetrated are torn away as the occlusion is pushed aside.

Another type of occlusion that may be difficult to treat with conventional procedures is hardened occlusions. Hardened occlusions may have a buildup of atherosclerotic plaque or other substances that is difficult to penetrate and/or dilate. A hardened occlusion is also a common condition of severe occlusions described above. For example, once an occlusion becomes completely occluded as in the case of a CTO, the upstream side of the occlusion often forms a fibrous, hardened cap that is difficult or impossible to penetrate with conventional devices. However, even partial occlusions where a conventional balloon catheter is passable may become so hardened that a conventional balloon cannot dilate the occlusion with conventional balloon pressures.

Accordingly, the inventors believe it would be desirable to provide a guidewire with an auger-like tip that could drill through an occlusion.

SUMMARY

A guidewire is described with an auger-like tip that may be used to drill through an occlusion. The guidewire has first and second helical members that cooperate in an enmeshed engagement. When a tubular member and a core member are rotated relative to each other, the second helical member extends from the first helical member to expose the second helical member at the distal end of the guidewire. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1A:
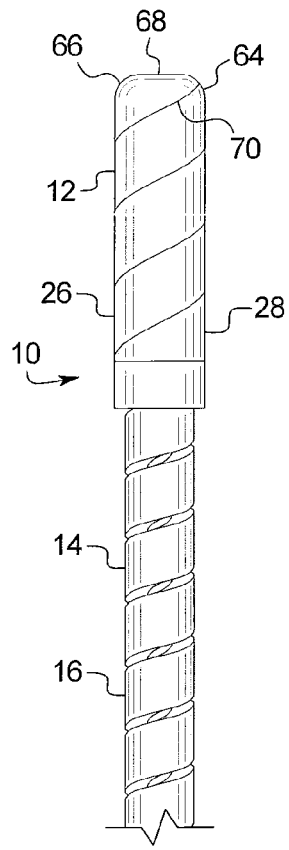
FIG. 1A is a side view of the distal end of a guidewire.
Figure 1B:
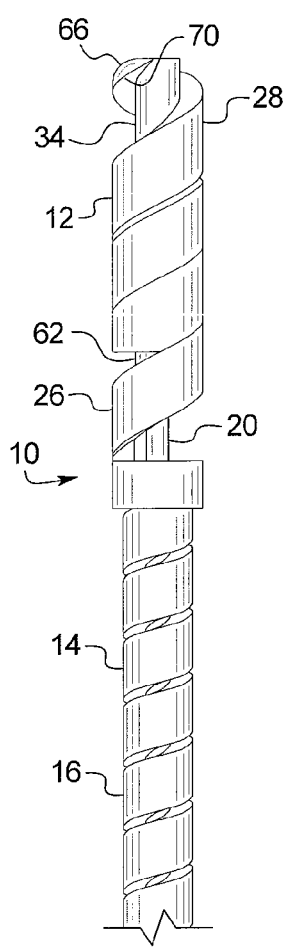
FIG. 1B is a side view of the distal end of the guidewire, showing the second helical member partially extended from the first helical member.
Figure 1C:
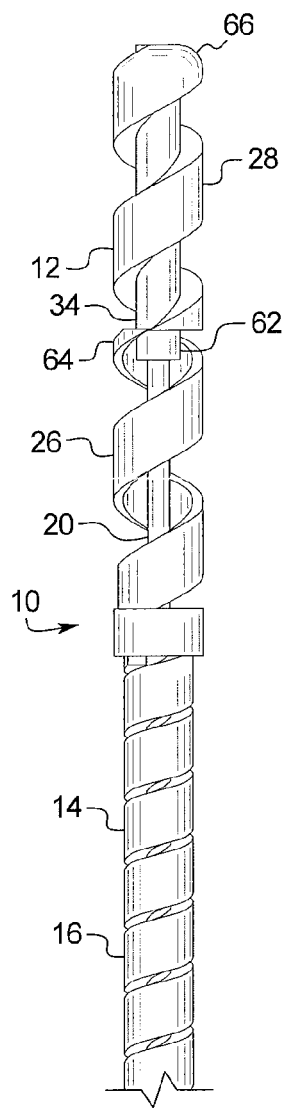
FIG. 1C is a side view of the distal end of the guidewire, showing the second helical member fully extended from the first helical member.
Figure 9:
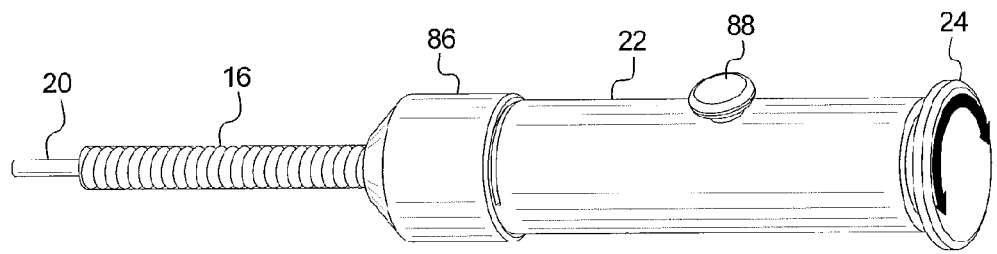
FIG. 9 is a side perspective view of the proximal end of the guidewire.
Figure 10:
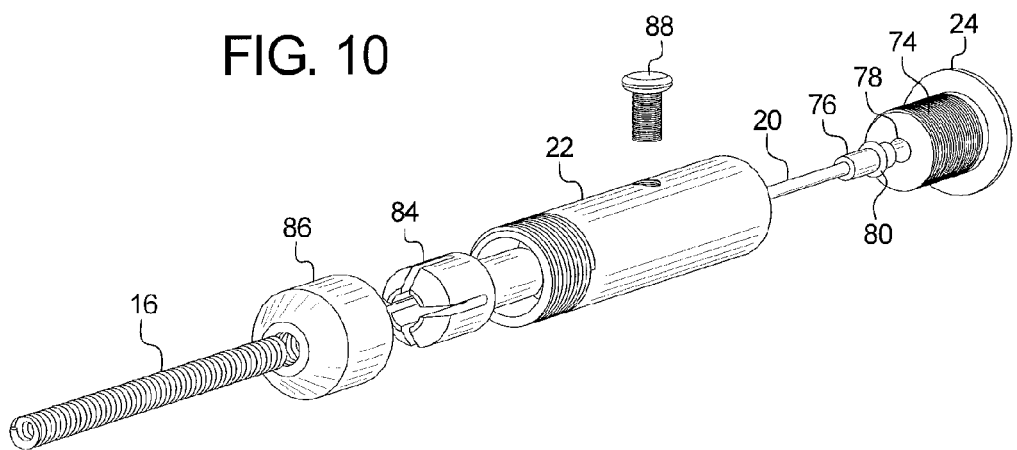
FIG. 10 is an exploded perspective view of the proximal end of the guidewire.
Figure 11:
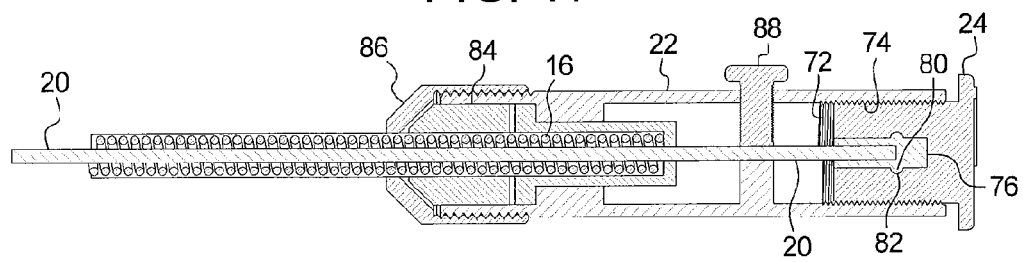
FIG. 11 is a cross-sectional view of the proximal end of the guidewire.

Referring now to the figures, and particularly to FIGS. 1A-1C, a guidewire 10 with an auger-like tip 12 is shown. The guidewire 10 has a body 14 that extends along the majority of the length of the guidewire 10 from the auger tip 12 to a proximal end. As better seen in FIGS. 5-6, the body 14 has an outer tubular member 16 with an axial lumen 18 extending therethrough. Preferably, the tubular member 16 is made of a coiled or braided structure, and most preferably, is made of a coil that is wound in the same helical direction as the first helical member 22. The body 14 also has a core member 20 extending coaxially through the lumen 18 of the tubular member 16. Preferably, the core member 20 has a solid interior without a lumen or space extending therethrough. As shown in FIGS. 9-11, the proximal end of the body 14 may have a first handle member 22 attached to the tubular member 16, and a second handle member 24 attached to the core member 20. The first and second handle members 22, 24 are preferably sized and shaped to allow a physician to manually manipulate the handle members 22, 24 in order to rotate the tubular member 16 and core member 20 relative to each other as they also move axially relative to each other.

Figure 3A:
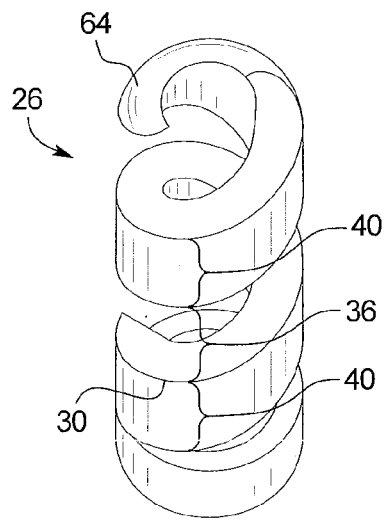
FIG. 3A is a perspective view of the first helical member.
Figure 3B:
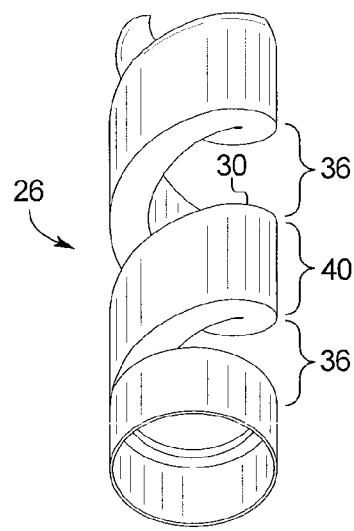
FIG. 3B is another perspective view of the first helical member.
Figure 4A:
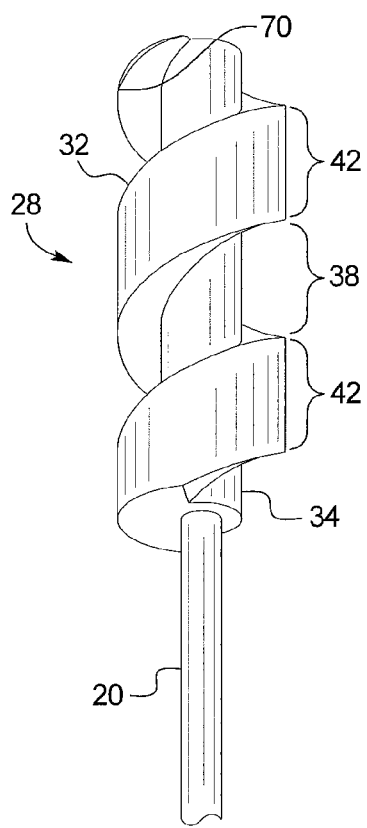
FIG. 4A is a perspective view of the second helical member.
Figure 4B:
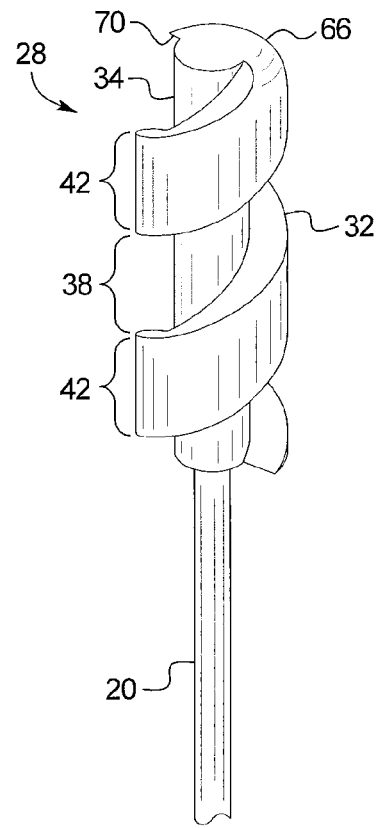
FIG. 4B is another perspective view of the second helical member.

The auger tip 12 includes a first helical member 26 attached to the distal end of the tubular member 16 and a second helical member 28 attached to the distal end of the core member 20. As better seen FIGS. 3A-4B, the first and second helical members 26, 28 each have a rib 30, 32 that winds around the axis of the guidewire 10 along a helical, or spiral, path. Preferably, the first and second helical members 26, 28 have a single helical rib 30, 32. As shown in FIGS. 3A-3B, the first helical member 26 is preferably hollow along the axis. By contrast, as shown in FIGS. 4A-4B, the second helical member 28 preferably has an axial shaft portion 34 that the helical rib 32 extends radially outward from. The shaft portion 34 may be sized to have an outer diameter that snugly fits within the inner surface of the hollow first helical member 26. Thus, the shaft portion 34 of the second helical member 28 and the inner surface of the first helical member 26 may guide the helical members 26, 28 relative to each other.

As shown in FIGS. 1A-1C, the auger tip 12 is movable between a retracted state (FIG. 1A) and an extended state (FIG. 1C). As noted above, this is accomplished by rotating the tubular member 16 and core member 20 relative to each other. Since the first and second helical members 26, 28 are engaged with each other in an enmeshed relationship, rotational movement of the tubular and core members 16, 20 causes the enmeshed engagement of the first and second helical members 26, 28 to drive against each other to move the first and second helical members 26, 28 rotationally and longitudinally. Thus, the helical members 26, 28 define a helical path that causes the first and second helical members 26, 28 to move longitudinally relative to each other when the tubular and core members 16, 20 are rotated relative to each other. Therefore, the first and second helical members 26, 28 simultaneously move rotationally and longitudinally relative to each other.

Preferably, the open regions 36, 38 between adjacent windings 40, 42 of the ribs 30, 32 of the first and second helical members 26, 28 have a width that is substantially the same as the width of the windings 40, 42 of the first and second helical members 26, 28. Thus, the ribs 30, 32 of the first and second helical members 26, 28 both have a shape that is generally the same as each other. Each of the ribs 30, 32 of the first and second helical members 26, 28 may also wind around the axis of the guidewire 10 at least one full revolution or more. Preferably, the ribs 30, 32 wind around the axis at least two full revolutions. Thus, when the first and second helical members 26, 28 are driven by rotating the tubular and core members 16, 20, the helical members 26, 28 remain enmeshed with each other for at least one full revolution, and preferably about two full revolutions.

Figure 5:
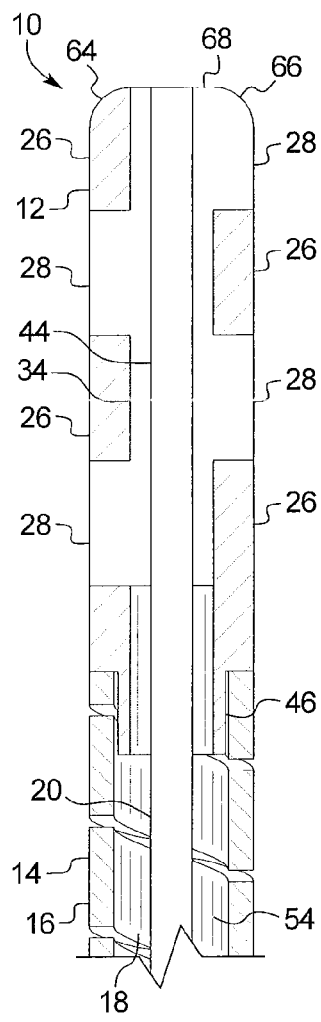
FIG. 5 is a cross-sectional view of a distal end of the guidewire.
Figure 6:
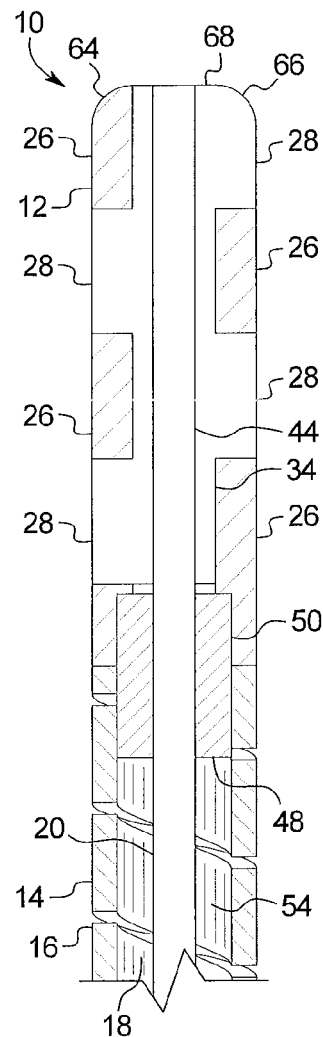
FIG. 6 is a cross-sectional view of another distal end of the guidewire.
Figure 7:
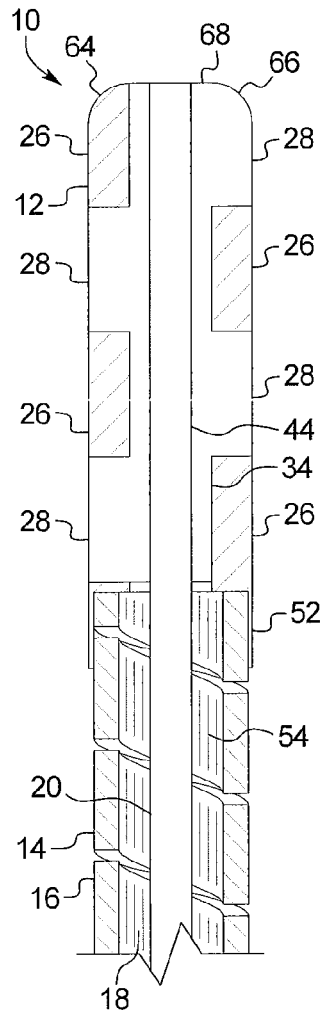
FIG. 7 is a cross-sectional view of another distal end of the guidewire.

As shown in FIGS. 5-7, the guidewire 10 may be constructed in numerous ways as desired. For example, in each of FIGS. 5-7, the core member 20 extends through an axial hole 44 in the shaft of the second helical member 28, and the core member 20 is secured to the shaft portion and second helical member 28 with soldering, welding, adhesives, etc. Alternatively, the core member 20 and second helical member 28 may be an integral single component, or the core member 20 and second helical member 28 may be attached at some other location, for example by butt welding them together or the like. In any event, the shaft portion 34 preferably has a solid interior without a lumen or space extending therethrough (that is, after the core member 20 and second helical member 28 are attached and the core member 20 fills the axial hole 44 if the design of FIGS. 5-7 is used).

The first helical member 26 may be attached to the tubular member 16 in various ways as illustrated in FIGS. 5-7. For example, in FIG. 5, the first helical member 26 may have a liner portion 46 that fits within the inner lumen 18 of the tubular member 16. Alternatively, in FIG. 6, a separate annular fitting 48 may be positioned in the inner lumen 18 of the tubular member 16, and the core member 20 may extend through the annular fitting 48. The annular fitting 48 may also extend into a hollow portion 50 of the first helical member 26. Further, in FIG. 7, the first helical member 26 may have a sheath portion 52 that fits around the outer surface of the tubular member 16.

Figure 8:
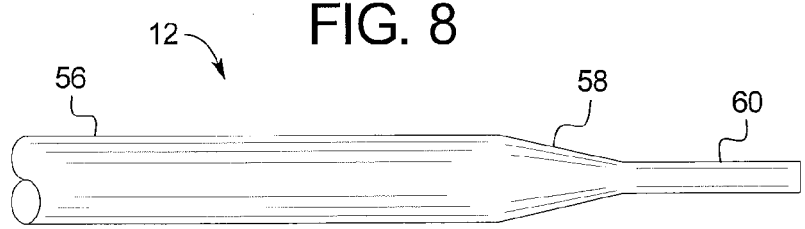
FIG. 8 is a side view of the distal end of the core member.

As shown in FIGS. 4A-7, the shaft portion 34 of the second helical member 28 is preferably larger in diameter than the core member 20. Moreover, as shown in FIGS. 5-7, there may be an annular space 54 between the core member 20 and the inner surface of the tubular member 16. With this construction, the body 14 may have a flexibility equivalent to a conventional guidewire, while the auger tip 12 is stiffer than the body 14 of the guidewire 10. However, the stiffness of the body 14 can be increased by increasing the diameter of the core member 20 if desired. For example, a manufacturer could provide different guidewires 10 with different stiffnesses by using core members 20 with different diameters and using the same tubular member 16 and auger tip 12. As shown in FIG. 8, the core member 20 may also have a larger diameter proximal portion 56, a tapered portion 58, and a smaller diameter distal end portion 60. This may be used in various ways to alter the stiffness of the guidewire 10. For example, the smaller diameter portion 60 may be inserted into the axial hole 44 in the second helical member 28 to attach the core member 20 to the second helical member 28, and the tapered portion 58 may provide a transition near the auger tip 12.

Alternatively, the smaller diameter portion 60 may extend proximally farther from the axial hole 44 in the second helical member 28 and may transition to the larger diameter portion 56 along a proximal section of the guidewire 10. This may make the guidewire 10 more stiff along the proximal section and more flexible along the distal section.

As shown in FIG. 1C, it may also be desirable for the shaft portion 34 of the second helical member 28 to extend proximally from the most proximal end of the helical rib 32. Thus, as shown in FIG. 1C, the proximal shaft portion 62 may remain within the hollow portion of the first helical member 26 when the second helical member 28 is fully extended to maintain guidance of the second helical member 28.

Figure 2:
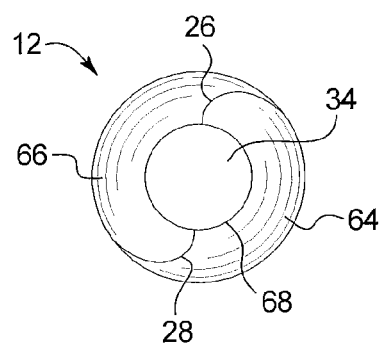
FIG. 2 is an end view of the distal tip of the guidewire.

As shown in FIGS. 1A and 2, the leading ends of the first and second helical members 26, 28 may have rounded edges 64, 66 around the outer circumference to form an atraumatic tip 68. As shown in FIG. 2, the leading ends of the first and second helical members may be designed so that they enmesh to form a contiguous distal end 68 in the retracted state. Thus, when the second helical member 28 is retracted, the distal end 68 of the guidewire 10 forms an atraumatic tip 68 similar to a conventional guidewire, which allows the guidewire 10 to be threaded through a patient's anatomy without traumatizing vessel walls. As shown in FIG. 1C, the distal end of the guidewire 10 may remain generally atraumatic when the second helical member 28 is extended since the second helical member 28 may have a rounded outer edge 66. The leading end of the second helical member 28 may also have a proximal edge 70 that is sharpened. This may allow the second helical member 28 to cut through tissue when the second helical member 28 is extended and rotated through an occlusion.

As shown in FIGS. 9-11, the guidewire 10 may be provided with a stop that limits longitudinal and rotational movement of the second helical member 28 when it reaches the fully extended state. Thus, when the physician rotates the first and second helical members 26, 28 relative to each other to extend the second helical member 28, the physician will eventually reach the stop at the fully extended state which prevents further movement between the first and second helical members 26, 28. Preferably, the stop may be designed so that the helical paths of the first and second helical members 26, 28 are generally aligned in the fully extended state as shown in FIG. 1C. Although the stop may be incorporated into the distal end of the guidewire, the stop is preferably provided at the proximal end of the guidewire 10 between the first and second handle members 22, 24. For example, as shown in FIGS. 9-11, the first and second handle members 22, 24 have threads 72, 74 that are threadably engaged. Thus, the stop may be the end of the threadable engagement, where the second handle member 24 is fully threaded into the first handle member 22 as shown in FIG. 11. However, in other embodiments, the stop may be where two flat surfaces abut each other or where a knob reaches the end of a slot. In the embodiment of FIGS. 9-11, the core member 20 is fixedly attached to an insert 76 that may be glued, pressed, or swaged onto the proximal end of the core member 20. The insert 76 may be pressed into an axial receiving hole 78 in the second handle 24. Once the insert 76 and the second handle member 24 are assembled together, the core member 20 and insert 76 are freely rotatable relative to the second handle member 24, but a circumferential rib 80 on the insert 76 and a circumferential recess 82 in the hole longitudinally fix the core member 20 and second handle member 24 together. The tubular member 16 is rotationally and longitudinally fixed to the first handle member 22 with a collet 84 that is squeezed onto the tubular member 16 by a cap 86 that is threaded onto the first handle member 22. Accordingly, when the first and second handle members 22, 24 are rotated relative to each other, the threads 72, 74 between the first and second handle members 22, 24 move the core member 20 and tubular member 16 longitudinally relative to each other. Since the core member 20 is freely rotatable within the second handle member 24, the first and second helical members 26, 28 at the distal are rotated relative to each other as they move longitudinally without binding against each other. The guidewire 10 is also preferably provided with a lock that is actuable by the physician at the proximal end, and allows the physician to extend the second helical member 28 at different lengths of extension relative to the first helical member 26. This allows the physician to change the level of extension before, during or after a procedure and lock the helical members in place during subsequent steps. For example, as shown in FIG. 11, the lock may be a screw 88 threaded through the first handle member 22 that engages the core member 20 to prevent relative movement of the core member 20. However, the lock may also take other forms if desired.

Although the guidewire 10 may be used for treating other medical conditions, a preferred medical procedure is the treatment of peripheral arterial disease occlusions. The guidewire 10 may also be especially useful for treating severe occlusions where it is difficult to push a conventional guidewire through the occlusion. For example, the Rutherford classification scale is one system for describing the different stages of peripheral arterial disease. Severe claudication corresponds to a Rutherford Stage 3 occlusion. Accordingly, it is believed that the guidewire 10 may be particularly useful for Rutherford Stage 3 or worse occlusions, since it may be difficult or impossible to gain access through severe occlusions like this with conventional guidewires. In addition, the guidewire 10 may be even more useful for chronic total occlusions where the artery is practically completely occluded. In these situations, the shape and structure of the occlusion makes it nearly impossible to push a conventional guidewire through the occlusion and typically requires a conventional guidewire to be pushed around the outside of the occlusion, and possibly through the tissues of the vessel wall. For peripheral arterial disease occlusions, it is preferred that the diameter of the guidewire 10 be about 0.012" to about 0.016", and the length of the guidewire 10 be at least 200 cm. Most preferably, the diameter of the guidewire 10 is about 0.014", and the length of the guidewire 10 is about 300 cm.

The guidewire 10 may be used in a similar fashion as a conventional guidewire in that the guidewire 10 may have an atraumatic tip 68; a diameter along its length that is equivalent to conventional guidewires; and pushability and torqueability equivalent to conventional guidewires. However, when the tip 68 of the guidewire 10 encounters an occlusion that conventional guidewires have difficulty traversing, the physician may extend the second helical member 28 by rotating the first and second handles 22, 24. The second helical member 28 may then penetrate the occlusion like a drill as the second helical member 28 extends from the first helical member 26. Alternatively, the physician may fully extend the second helical member 28 before penetrating the occlusion, and then rotate both handles 22, 24 together to drill the first and second helical members 26, 28 through the occlusion, with the second helical member 28 leading the first helical member 26. The guidewire 10 may then be used to clear the occlusion by pulling the first and second helical members 26, 28 through the occlusion and aspirating debris from the occlusion with an aspirating catheter disposed over the guidewire 10 and adjacent the occlusion. The guidewire 10 may also be used in a more conventional manner at this stage as a trackway for other medical devices specifically designed to clear or dilate the occlusion.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A guidewire, comprising:
   a tubular member extending from a proximal end to a distal end and comprising a lumen extending therethrough;
   a core member extending from a proximal end to a distal end and disposed within said lumen of said tubular member;
   a first helical member attached to said distal end of said tubular member; and
   a second helical member attached to said distal end of said core member;
   wherein said first and second helical members cooperate in an enmeshed engagement, said first and second helical members being longitudinally moveable relative to each other by rotating said core member and said tubular member relative to each other, said enmeshed engagement thereby driving said first and second helical members along a rotational and longitudinal path; and
   wherein said first and second helical members are rotatable relative to each other at least one full revolution while remaining enmeshed with each other.

2. The guidewire according to claim 1, wherein each of said first and second helical members are defined by respective open regions disposed between adjacent windings of said first and second helical members, a width of said open regions of said first and second helical members and a width of said windings of said first and second helical members being substantially the same, the shape of said first and second helical members thereby being generally the same.

3. The guidewire according to claim 1, wherein each of said first and second helical members comprise a single helical rib.

4. The guidewire according to claim 1, wherein said core has a solid interior.

5. The guidewire according to claim 1, further comprising a shaft portion attached to said core member and said second helical member, said shaft portion having an outer diameter sized to fit within an inner surface of said first helical member to thereby guide said first and second helical members relative to each other.

6. The guidewire according to claim 5, wherein said shaft portion is larger in diameter than said core member.

7. The guidewire according to claim 6, wherein said shaft portion extends proximally past said second helical member, said shaft portion thereby remaining within said inner surface of said first helical member when said second helical member is completely extended from said first helical member to thereby guide said second helical member.

8. The guidewire according to claim 5, wherein said shaft portion has a solid interior.

9. The guidewire according to claim 1, wherein a proximal edge of a leading end of said second helical member is sharpened to cut through tissue when said second helical member is rotated through said tissue.

10. The guidewire according to claim 1, wherein a leading end of said second helical member has a rounded edge around an outer circumference thereof.

11. The guidewire according to claim 1, wherein leading ends of said first and second helical members are enmeshable to form a contiguous distal end of said guidewire in a retracted state, said leading ends having corresponding rounded edges around an outer circumference thereof to form an atraumatic tip of said guidewire.

12. The guidewire according to claim 1, further comprising a stop that limits longitudinal and rotational movement of said second helical member relative to said first helical member in a fully extended state.

13. The guidewire according to claim 12, wherein helical paths of said first and second helical members are generally aligned in said fully extended state.

14. The guidewire according to claim 1, said tubular member comprises a coil or a braid.

15. The guidewire according to claim 14, wherein said tubular member comprises a coil wound in a same helical direction as said first helical member.

16. The guidewire according to claim 1, wherein each of said first and second helical members are defined by respective open regions disposed between adjacent windings of said first and second helical members, a width of said open regions of said first and second helical members and a width of said windings of said first and second helical members being substantially the same, the shape of said first and second helical members thereby being generally the same, each of said first and second helical members comprise a single helical rib, and said core has a solid interior.

17. The guidewire according to claim 16, further comprising a shaft portion attached to said core member and said second helical member, said shaft portion having an outer diameter sized to fit within an inner surface of said first helical member to thereby guide said first and second helical members relative to each other, said shaft portion has a solid interior, and said tubular member comprises a coil or a braid.

18. The guidewire according to claim 17, wherein leading ends of said first and second helical members are enmeshable to form a contiguous distal end of said guidewire in a retracted state, said leading ends having corresponding rounded edges around an outer circumference thereof to form an atraumatic tip of said guidewire, further comprising a stop that limits longitudinal and rotational movement of said second helical member relative to said first helical member in a fully extended state, and wherein helical paths of said first and second helical members are generally aligned in said fully extended state.

19. A guidewire, comprising:
   a tubular member extending from a proximal end to a distal end and comprising a lumen extending therethrough;
   a core member extending from a proximal end to a distal end and disposed within said lumen of said tubular member;
   a first helical member attached to said distal end of said tubular member; and
   a second helical member attached to said distal end of said core member;
   wherein said first and second helical members cooperate in an enmeshed engagement, said first and second helical members being longitudinally moveable relative to each other by rotating said core member and said tubular member relative to each other, said enmeshed engagement thereby driving said first and second helical members along a rotational and longitudinal path; and wherein each of said first and second helical members are defined by respective open regions disposed between adjacent windings of said first and second helical members, a width of said open regions of said first and second helical members and a width of said windings of said first and second helical members being substantially the same, the shape of said first and second helical members thereby being generally the same.

20. The guidewire according to claim 19, wherein said first and second helical members are rotatable relative to each other at least one full revolution while remaining enmeshed with each other.

\* \* \* \* \*